United States Patent [19]

Ayers et al.

[11] Patent Number: 4,603,010

[45] Date of Patent: Jul. 29, 1986

[54] LIPOPROTEIN FRACTIONATION

[76] Inventors: John S. Ayers; William S. Hancock; David R. K. Harding, all c/o Massey University, Palmerston North, New Zealand

[21] Appl. No.: 736,306

[22] Filed: May 21, 1985

[30] Foreign Application Priority Data

May 22, 1984 [NZ] New Zealand .................. 208241

[51] Int. Cl.$^4$ ............................................. C07K 15/16
[52] U.S. Cl. ................................... 530/359; 424/101; 514/2; 514/8; 530/416
[58] Field of Search ............... 260/112 B; 424/101; 514/2, 8

[56] References Cited

U.S. PATENT DOCUMENTS 4,096,136 6/1978 Ayers et al. ................. 260/112 B
4,178,439 12/1979 Ayers et al. ...................... 536/59

OTHER PUBLICATIONS

The Lancet (Jun. 12, 1976), 1261–1265, Lupien et al.
Pediat. Res. 14: 113–117 (1980), Lupien et al.

Primary Examiner—Howard E. Schain
Attorney, Agent, or Firm—Holman & Stern

[57] ABSTRACT

A process is described for removing low density and very low density lipoproteins from blood plasma or serum and recovering the plasma or serum in a physiologically acceptable form. The method involves in a preferred embodiment passing plasma or serum through a cationic ion exchanger equilibrated with a physiologically acceptable saline solution. The ion exchanger is a water insoluble hydrophilic, water swellable cross-linked regenerated or microgranular cellulose matrix substituted with hydroxy $C_2$–$C_4$ alkyl group. The ion exchanger capacity is provided by sulphate groups substituted with from 2 to 6 meq/g. The take up of low density lipoproteins is enhanced by recycling the plasma through the column.

10 Claims, 6 Drawing Figures

LIPOPROTEIN FRACTIONATION

FIELD OF INVENTION

This invention relates to a method of purifying blood plasma or serum by selective removal of low density lipoproteins and very low density lipoproteins.

BACKGROUND OF THE INVENTION

Lipoproteins in fasting plasma comprise three primary fractions: the very low density (VLDL) fraction, the low density (LDL) fraction, and the high density (HDL) fraction. It has been observed that a high VLDL+LDL:HDL ratio is associated with a correspondingly high incidence of premature coronary artery disease. ("The Low Density Lipoprotein Pathway and its Relation to Atherisochlerosis", J. L. Goldstein, and M. S. Brown 1977. *Annual Review of Biochemistry* 46:897-930). Furthermore, an inverse relation has been observed between a high HDL:VLDL+LDL ratio and total mortality due to cardiovascular disease. ("Associations of Serum High Density Lipoprotein and Total Chloesterol with Total Cardiovascular and Cancer Mortality in a Seven Year Prospective Study of 10,000 Men.", S. Yaari, U. Goldbourt, S. Ivan-Zohar and H. W. Nerifeld 1981. *Lancet* 1:1011-1015).

It is known in the art that lipoproteins can be removed selectively from blood plasma or serum by the use of a sulphated ion exchanger. In U.S. Pat. No. 4,096,136 dated June 20, 1978 there is described an in vitro treatment of blood serum of plasma for selective removal of lipoprotein fractions for analytical purposes. Lipoproteins are selectively bound in the presence of other plasma or serum proteins and ions. The process involves the equilibration of the sulphated ion exchanger in a column with a solution containing a divalent cation, and the addition of the same cation to the plasma or serum to adjust the divalent cation concentration of the plasma or serum to between 0.05 and 1.0M. The plasma or serum is then passed through the equilibrated column where the the lipoproteins are selectively bound and the other components remain in the plasma or serum. The bound lipoproteins are eluted from the column and the proportion of LDL, VLDL and HDL is determined. The greater the proportional amount of the LDL and VLDL, the more a patient is at risk.

The method of U.S. Pat. No. 4,096,136 is an analytical one. It would be desirable to be able to extract selectively the LDL and VLDL fraction while leaving the HDL in plasma or serum and then reuse the plasma or serum. The process of U.S. Pat. No. 4,096,136 is not physiologically acceptable because of the inherent toxicity of the divalent cation used in the first step. Any blood so treated would be physiologically incompatible.

It has now unexpectedly been found that by employing a sulphated ion exchanger having a relatively high degree of substitution it is possible to bind the LDL and VLDL fractions without the use of a relatively high concentration of divalent cations in the equilibrating solution. In addition HDL is not retained, thus use of the column allows maximum adjustment of the HDL:LDL+VLDL ratio.

It is an object of this invention to go some way toward achieving this desideratum, or at least to offer the public a useful choice.

SUMMARY OF THE INVENTION

The invention may be said broadly to consist in a method of preparing blood plasma or serum with reduced LDL and VLDL content, comprising the steps of:

(a) associating blood plasma or serum with a cationic ion exchanger equilibrated with a physiologically acceptable saline solution, said exchanger comprising a water insoluble, hydrophilic, water swellable cross-linked regenerated or microgranulated cellulose matrix substituted with hydroxy $C_2$-$C_4$ alkyl groups and having at least 2 meq./gm sulphate groups chemically bonded to said matrix, the ion exchanger capacity of said exchanger being provided by said sulphate groups; and (b) recovering said blood plasma or serum from said ion exchanger after a portion of said LDL and VLDL fractions have been extracted therefrom by said ion exchanger.

Preferably, the degree of sulphation of said ion exchanger is at least 5.0 meq./gm.

Preferably, said physiologically acceptable saline solution has the composition:
100–160 mM NaCl
0–40 mM NaHCO$_3$
2–8 mM KCl
1–6 mM MgCl$_2$ More preferably said physiologically acceptable saline solution has the composition:
142 mM NaCl
5 mM KCl
3 mM MgCl$_2$ Most preferably said physiologically acceptable saline solution has the composition:
115 mM NaCl
27 mM NaHCO$_3$
5 mM KCl
3 mM MgCl$_2$ Preferably said hydroxy $C_2$-$C_4$ alkyl group is an hydroxy propyl group.

Preferably said step of associating blood or blood plasma with a cationic ion exchanger comprises passing said blood through at least one column packed with said cationic exchanger.

Preferably said regenerated cellulose matrix is cross-linked with epichlorohydrin and has pendant hydroxy propyl groups bonded thereto.

Preferably said blood plasma or serum passed through said column is passed through said column at least twice.

Preferably said blood plasma or serum passed through said column is passed through said column at least three more times.

The invention consists in the foregoing and also envisages embodiments of which the following gives examples.

BRIEF DESCRIPTION OF THE DRAWINGS

The invention may be more fully understood by having reference to the accompanying drawings, wherein.

DETAILED DESCRIPTION OF THE INVENTION

Figure 1:
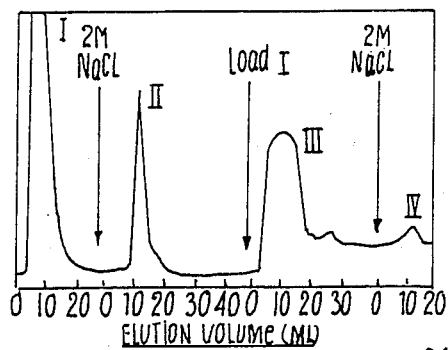
FIG. 1 is an elution profile showing the LDL and VLDL capacity of sulphated hydroxypropylated regenerated cellulose when equilibrated with physiological saline buffer.

The invention may be more completely understood by having reference to the following examples.

EXAMPLE 1

Preparation Of Resin (a) Preparation of hydroxypropylated regenerated cellulose

The title compound was prepared in accordance with the procedure of example 3 of U.S. Pat. No. 4,178,439.

(b) Preparation of 2 meq/g resin

Hydroxypropylated regenerated cellulose from (a) (10 g) was mixed with 110 ml of dimethylformamide (DMF) overnight to swell the matrix (achieved by placing in a sealed bottle rotated on a rolling bar). Pyridine-chlorosulphonic acid complex (10 g) was added and the mixture was rolled for 40 H. The product was filtered using vacuum to a moist cake which was then washed with the following solvents—DMF (200 ml), DMF:H$_2$O, 50:50 (200 ml), H$_2$O (500 ml), 1M NaCl (500 ml in 4 portions), and water (500 ml in 4 portions). The resin was then defined and freeze dried.

(c) Preparation of 5 meq/g resin

The same procedure as in (b) was followed except that 40 g of complex and 120 ml of DMF were used with a 10 g sample of resin.

EXAMPLE 2

Preparation of Physiological Saline Buffer (pH 7.4)

The buffer was prepared with the following concentrations of solutes. NaCl (142 mM), KCl (5 mM) and MgCl$_2$ (3 mM). This corresponds to the ionic composition of plasma:

| cations | mM | anions | mM |
|---|---|---|---|
| Na$^+$ | 142 | HCO$_3^-$ | 27 |
| K$^+$ | 5 | CL$^-$ | 103 |
| Ca$^{2+}$ | 5* | phosphate | 2 |
| Mg$^{2+}$ | 3 | protein | 16 |

*The Ca$^{2+}$ was omitted from the buffer because it promoted clotting of the plasma.

(Reference J. L. Gamble, Chemical Anatomy, Physiology and Pathology of Extracellular Fluid, 6th Edn., Harvard Univ. Press, 1954.)

To prepare 4 l of this buffer 20 ml of 1M KCl, 6 ml of 2M MgCl$_2$ and 142 ml of 4M NaCl were made up to the required volume.

EXAMPLE 3

Preparation Of Mg$^{2+}$-Containing Buffer (pH 7.4)

The composition of the buffer was MgCl$_2$ (0.25M), NaCl (0.02M), and NaHCO$_3$ (0.1M). To prepare 1 l of this buffer the following amounts were dissolved: MgCl$_2$.6H$_2$O (50.82 g), NaCl (1.2 g), NaHCO$_3$ (0.84 g).

EXAMPLE 4

Preparation Of Elution Buffer (pH 7.4)

The composition of the buffer was NaCl (2M) and NaHCO$_3$ (0.01M). To prepare the buffer the following amounts were dissolved in 1 l of water-sodium chloride (117 g), NaHCO$_3$ (0.84 g).

EXAMPLE 5

Buffer Added to Plasma To Adjust Sample To Concentration Of The Mg$^{2+}$-Containing Buffer The buffer contained 25 ml of 2M MgCl$_2$, 4 ml. of 1M NaCl and 2 ml of 1M NaHCO$_3$. The pH was adjusted to 7.4 and volume made up to 100 ml. The plasma was diluted 1:1 with this buffer.

EXAMPLE 6

Buffer Used To Clean Resin And Procedure For Removing Fines

Resins prepared according to Example 1 were washed successively with 10 column volumes of 3M NaCl, 0.1M ammonium carbonate, pH 9.0, then distilled water, then water:ethanol, 2:1 and finally distilled water. Some fine particles were generated during column use and regeneration and were removed by allowing the resin to settle in a tall vessel (e.g. measuring cylinder). The excess liquid containing the fines (at least 25% of the volume of the resin) was removed by suction.

EXAMPLE 7

Preparation Of Plasma Sample

During collection of porcine blood, 5 g/l of sodium citrate was added to prevent clotting. The blood was then centrifuged at 4,000 rpm for 20 min to remove the red blood cells. If necessary the pH of the plasma sample was adjusted to 7.4 with either 0.13M NaOH or 0.1HCl. The conductivity was adjusted to 6.5 mΩ for experiments with the physiological saline buffer and 16 mΩ for experiments with Mg$^{2+}$-containing buffer (with either water or 1–4M NaCl depending on the sample). For the separations with the Mg$^{2+}$-containing buffer the plasma sample was mixed 1:1 with a buffer prepared in accordance with Example 5.

EXAMPLE 8

Chromatographic Conditions

Resin samples (5 ml, swollen volume 14 ml/g, 5.16 meq/g) made in accordance with Example 1 were equilibrated with the column buffer and pH and conductivity of the effluent were measured. Before use in test columns the resin was exposed to a plasma sample and then cleaned. This pre-treatment of the resin substantially reduced loss of material that was observed when a resin sample was used for the first time. The resin samples were packed into glass columns (0.9×20 cm) with a glass wool plug to retain the resin. The flow rate used was 1.6 ml/min and was achieved with a peristaltic pump. The fractions were monitored on a Cecil 212 spectrophotometer at 2 O.D. full scale. The wavelength used was either 242 or 256 nm for the physiological saline runs or 300 nm for the $Mg^{2+}$-containing buffer. The chart recorder was run at 0.25 cm/min.

EXAMPLE 9

Measurement Of VLDL, LDL Capacity OF Resin When Equilibrated With Physiological Saline Buffer A series of test columns containing 5 ml of resin prepared according to Example 1 were equilibrated with physiological saline buffer and loaded with the following plasma volumes 0.5, 1.0, 1.5, 2.0, 2.5, 3.0, 4.0 and 10 ml. After loading, each column was washed with physiological saline buffer until the O.D. readings returned to initial values (peak I in FIGS. 1, 3 and 6). This washing solution was collected. The elution buffer was then used to elute the bound VLDL+LDL fraction (peak II in FIGS. 1, 3 and 6). The collected solution correspondinhg to Peak I was then loaded on a second test column, also equilibrated with physiological saline buffer, and the loadings were repeated to give peak III (unbound material) and peak IV (residual VLDL, LDL which did not bind to the first column).

A typical elution profile for the chromatography series is shown as FIG. 1. This profile shows that the majority of the VLDL and LDL present in blood is bound by one passage of the blood through the resin.

Figure 2:
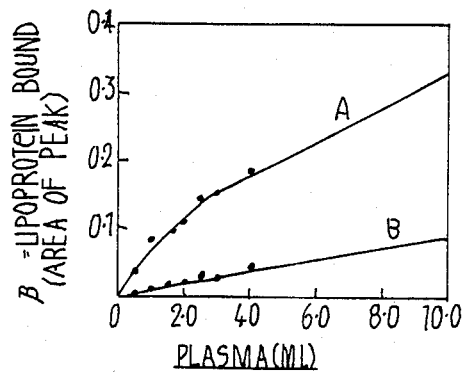
FIG. 2 is a plot of the areas of peaks II and IV (A and B respectively) of LDL and VLDL bound to 5 ml columns of sulphated hydroxypropylated regenerated cellulose against volumes of plasma passed through the column.

This result is more clearly shown in FIG. 2, where the combined amount of VLDL and LDL bound at the different plasma loadings of the example is shown. Curve A corresponds to the amount of combined VLDL and LDL bound to the first column, whereas curve B shows the combined amount of VLDL and LDL bound when the collected solution corresponding to Peak I was loaded onto the second column. Thus at a loading of 10 ml of plasma for a 5 ml. column, 79% (0.33 out of a total of 0.40 g) of the VLDL and LDL was removed by a single passage through the column.

A relatively high flow rate was used in these experiments (linear velocity of 1.8 cm/min) and this would explain the incomplete binding of lipoproteins even at low sample loadings. These high flow rates were chosen to approximate clinical conditions where the separation must be carried out in the minimum time (e.g. 1400 ml of resin packed in a column of 10 cm diameter gives a flow rate of 200 ml/min (12 l/ hour) which corresponds to the flow rate used in the test column).

EXAMPLE 10

Measurement Of The Total Lipoprotein Capacity Of Sulphated Resin When Equilibrated With $Mg^{2+}$-Containing Buffer A chromatography series using test columns equilibrated with $Mg^{2+}$ buffer was run for the purpose of comparison.

Plasma samples prepared as in Example 7 were chromatographed using the experimental conditions described in Example 9, except that the columns were equilibrated with a $Mg^{2+}$-containing buffer. For each separation with $Mg^{2+}$-containing buffer, plasma loading volumes were mixed in a 1:1 ratio with the buffer of Example 5.

Figure 3:
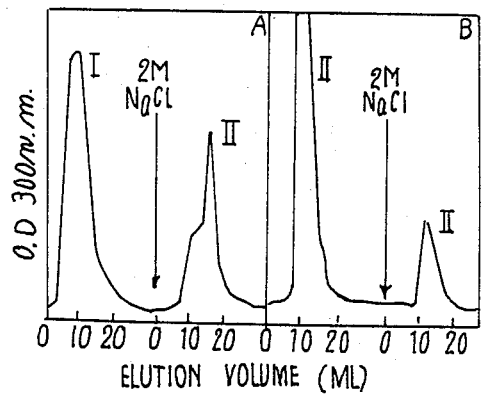
FIG. 3A is an elution profile of total LDL, VLDL and HDL bound from a 1 ml. plasma sample using a sulphated hydroxypropylated regenerated cellulose equilibrated with $Mg^{2+}$ containing buffer.
FIG. 3B is an elution profile of total LDL and VLDL bound from a 1 ml plasma sample using a sulphated hydroxypropylated regenerated cellulose equilibrated with physiologically saline buffer.
Figure 4:
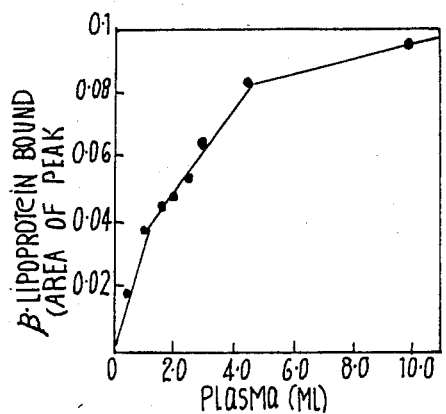
FIG. 4 is a plot as in FIG. 2 but with the column equilibrated with $Mg^2$ buffer.

FIG. 3 compares the elution profiles of the two chromatography series. FIG. 3A shows a typical elution profile for the series of Example 10, with Peak II now containing VLDL, LDL and HDL. FIG. 3B shows the profile for the series of Example 9 conducted in the substantial absence of $Mg^{2+}$. This effect is also illustrated by comparison of FIG. 2 with FIG. 4.

Figure 5:
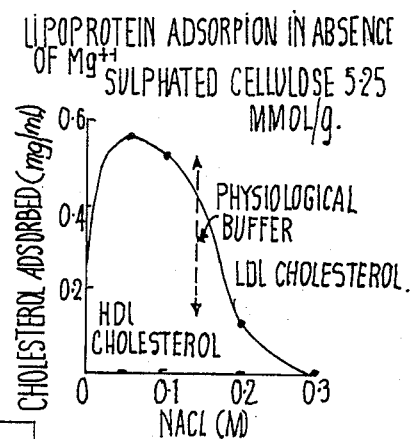
FIG. 5 is a plot of cholesterol absorbed in mg/ml against concentration of NaCl in a physiological buffer showing the relative amounts of LDL and HDL fractions which are bound.

It can be seen that the removal of $Mg^{2+}$ from the column results in much less total lipoprotein being bound. This decrease in binding is due to HDL not being retained by the matrix equilibrated with physiological saline. The lack of binding of HDL is also shown in more detail in FIG. 5.

EXAMPLE 11

Figure 6:
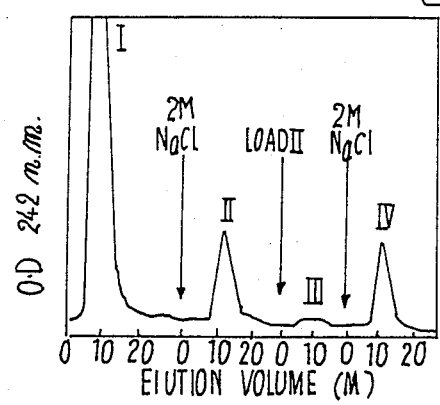
FIG. 6 is an elution profile showing the amount of non-specific binding of other serum proteins to sulphated hydroxypropylated regenerated cellulose when equilibrated with physiological saline buffer.

Measurement Of The Amount Of Non-Specific Binding To Sulphated Resin When Equilibrated With Physiological Saline Buffer Under the experimental conditions of Example 9, the same plasma loading volumes as in Example 9 were chromatographed. The combined LDL and VLDL solution corresponding to Peak II was collected and reloaded onto a second column also equilibrated with physiological saline. The effect of this reloading is shown in FIG. 6.

Control experiments indicated that other major serum proteins do not bind to the sulphated resin. However, a small amount of some proteins can contaminate the bound lipoprotein due to binding to the lipoprotein-resin complex. Thus, in FIG. 6, the amount of protein in each of Peaks II and IV was measured by the Lowry method (Lowry, 1951, Biol. Chem., 193, p 265 et seq.) and the amount of contamination (as measured by loss of protein in Peak IV relative to Peak II) was less than 3%. This value corresponded to the small decrease in area of Peak IV relative to Peak II.

This result indicates that the use of this resin equilibrated with a physiologically acceptable level of saline to remove LDL from patients' blood will result in the loss of only very small amounts of serum proteins e.g. albumin, globulins. It is possible that some serum proteins such as factor 8, that are known to bind to heparin affinity columns, will however be removed.

EXAMPLE 12

Alternative Preparation Of Sulphate Resin

| A. $SO_3$:DMF | Complex preparation |
| --- | --- |

A solution of (dimethyformamide) DMF:$SO_3$ was prepared by slowly dripping liquid $SO_3$ (100 ml) into well stirred, chilled (0°–4° C.) DMF (2 l). The temperature was maintained at 0°–4° C. throughout the addition and the solution stirred to room temperature for 1 hour on completion of the $SO_3$ addition. The resulting solution was stored in ground glass stoppered brown jars, under nitrogen and in the dark. A sample of the solution was diluted with water and titrated-result a 1.18N solution of $SO_3$:DMF.

B. Sulphation (a) Initial 1 g experiments showed that 5.5 ml of the above solution with hydroxypropylated regenerated cellulose (resin) gave a sulphate substitution of about 1.5 meq/g and a swollen volume of 19 ml/g. Using 16 mls of this solution gave 4.9 meq/g and 16 ml/g respectively. Use of this sulphation procedure was accompanied by addition of one equivalent of pyridine as outlined below.

(b) Procedure.

100 g of resin was swollen in 700 ml DMF overnight, 175 ml pyridine was added to 1750 ml $SO_3$:DMF complex, this mixture was then added to the swollen DMF-resin suspension, the resulting mixture was then stirred for six hours in a closed container and left to stand overnight, the resin was washed as follows: 2 liters DMF; 3 liters 70% DMF/30% $H_2O$; 3 liters 30% DMF/70% $H_2O$; 17 L $H_2O$, the resulting material was freeze dried and gave 5.35 meq/g and weighed 190 g (swollen volume 14 ml/g), a scale up to 450 g of resin gave similar results.

EXAMPLE 13

Cholesterol Capacity

Resin was prepared in accordance with the procedure in Example 12.

The column volume was 7.5 ml after equilibrating with buffer. It was loaded with 37 ml of serum (ratio 5:1) which was diluted with 0.5 ml 1M $NaHCO_3$
1.0 ml 1M NaCl
distilled water to a
Total Volume: 70 ml 3 Columns were set up:
1. Sulphated hydroxypropylated microgranular cellulose (SMGC) equilibrated with physiological buffer.
2. Sulphated hydroxypropylated regenerated cellulose (SHRC) equilibrated with $Mg^{+2}$ containing buffer, washed with saline.
3. SHRC was Equilibrated with physiological buffer, washed with saline.

Samples were loaded and run through slowly 4 times (less than 1.5 ml/min) and analysed at Palmerston North Hospital, Palmerston North, New Zealand.

| Cholesterol analyses. | Mg (mmol/l) | Chol (mmol/l) |
| --- | --- | --- |
| Total serum | 0.76 | 6.4 |
| S.M.G.C. | 0.24 | 2.0 |
| S.H.R.C. (physio buffer) | 0.29 | 2.4 |
| S.H.R.C. ($Mg^{+2}$ cont buffer) | 1.07 | 2.6 |
| Cholesterol Capacities of the Resin | | g/l |
| 1. (SMGC) | | 8.5 |
| 2. (SHRC) (physio buffer) | | 8.0 |
| 3. (SHRC) ($Mg^{+2}$ cont buffer) | | 7.3 |

The procedure was repeated except that the sample was diluted with water only with the following results:

| | Mg (mmol/l) | Chol (mmol/l) |
| --- | --- | --- |
| Total serum | 0.89 | 8.1 |
| (SHRC Mg buffer) | 0.33 | 2.9 |
| (SHRC physio buffer) | 0.27 | 2.6 |
| Cholesterol Capacities of the Resin | | |
| 1. (SHRC Mg buffer) | | 10.1 g/l |
| 2. (SHRC physio buffer) | | 10.1 g/l |

The cholesterol capacity is directly proportional to the VLDL+LDL capacity of the resin. It will be seen that use of the method with a physiologically acceptable buffer gives results at least equivalent to that using a $Mg^{+2}$ buffer. In addition dilution of the sample with water instead of buffer leads to a higher capacity.

What we claim is:

1. A method of reducing LDL and VLDL content in blood plasma or serum, consisting essentially of the steps of:
   (a) associating blood plasma or serum with a cationic ion exchanger equilibrated with a physiologically acceptable saline solution, said exchanger comprising a water insoluble, hydrophilic, water swellable cross-linked regenerated or microcellular cellulose matrix substituted with hydroxy $C_2$-$C_4$ alkyl groups and having at least 2 meq./gm sulphate groups chemically bonded to said matrix, the ion exchange capacity of said exchanger being provided by said sulphate groups; and
   (b) recovering said blood plasma or serum from said ion exchanger after a portion of said LDL and VLDL fractions have been extracted therefrom by said ion exchanger.

2. A method according to claim 1 wherein the degree of sulphation of said ion exchanger used is from 4 to 6.0 meq./gm.

3. A method according to claim 1 wherein said physiologically acceptable saline solution used has the composition:
   100-160 mM NaCl,
   0-40 mM $NaHCO_3$,
   2-8 mM KCl,
   1-6 mM $MgCl_2$.

4. A method according to claim 2 wherein said physiologically acceptable saline solution used has the composition:
   142 mM NaCl,
   5 mM KCl,
   3 mM $MgCl_2$.

5. A method according to claim 2 wherein said physiologically acceptable saline solution used has the composition:
   115 mM NaCl,
   27 mM $NaHCO_3$,
   5 mM KCl,
   3 mM $MgCl_2$.

6. A method according to claim 1 wherein said hydroxy $C_2$-$C_4$ alkyl group is an hydroxy propyl group.

7. A method according to claim 1 wherein said step of associating blood plasma or serum with a cationic ion exchanger comprises passing said blood plasma or serum through at least one column packed with said cationic exchanger.

8. A method according to claim 1 wherein said cellulose matrix used is regenerated cellulose cross-linked with epichlorohydrin and has pendant hydroxy propyl groups bonded thereto.

9. A method according to claim 7 wherein said blood plasma or serum passed through said column is passed through said column at least twice more.

10. A method according to claim 7 wherein said blood plasma or serum passed through said column is passed through said column at least three more times.

* * * * *